United States Patent [19]

Gessler et al.

[11] Patent Number: 5,061,237
[45] Date of Patent: Oct. 29, 1991

[54] METHOD OF PURIFYING WHOLE BLOOD

[75] Inventors: Reiner Gessler, Aschaffenburg; Manfred Rycyk, Koerle, both of Fed. Rep. of Germany

[73] Assignee: Cytomed Medizintechnik GmbH, Aschaffenburg, Fed. Rep. of Germany

[21] Appl. No.: 420,770

[22] Filed: Oct. 11, 1989

Related U.S. Application Data

[63] Continuation of Ser. No. 220,880, Jun. 22, 1988, abandoned, which is a continuation of Ser. No. 881,416, Jul. 2, 1986, abandoned.

[30] Foreign Application Priority Data

Jul. 2, 1985 [DE]  Fed. Rep. of Germany ....... 3523615
Jul. 2, 1985 [DE]  Fed. Rep. of Germany ....... 3523616

[51] Int. Cl.$^5$ ............................................ A61M 37/00
[52] U.S. Cl. ......................................... 604/5; 436/512
[58] Field of Search ........................................ 604/4–6, 604/264–265; 436/512, 528, 531

[56] References Cited

U.S. PATENT DOCUMENTS

| | | | |
|---|---|---|---|
| 4,272,504 | 6/1981 | Kim et al. | 436/825 |
| 4,279,885 | 7/1981 | Reese et al. | 436/518 |
| 4,292,403 | 9/1981 | Duermeyer | 435/5 |
| 4,374,925 | 2/1983 | Litman et al. | 435/7 |
| 4,425,438 | 1/1984 | Bauman et al. | 436/824 |
| 4,478,946 | 10/1984 | Van der Merve et al. | 436/518 |
| 4,552,839 | 11/1985 | Gould et al. | 436/824 |
| 4,624,930 | 11/1986 | Tanswell et al. | 436/824 |
| 4,632,901 | 12/1986 | Valkirs et al. | 436/824 |
| 4,634,417 | 1/1987 | Korec | 604/6 |
| 4,664,913 | 5/1987 | Mielke et al. | 604/6 |

FOREIGN PATENT DOCUMENTS

| | | | |
|---|---|---|---|
| 0082345 | 6/1983 | European Pat. Off. | 604/5 |
| 0109531 | 5/1984 | European Pat. Off. | 604/5 |
| 0138297 | 6/1984 | European Pat. Off. | |
| 0132534 | 2/1985 | European Pat. Off. | 604/4 |
| 0151357 | 11/1981 | Japan | 436/518 |
| 0170263 | 10/1982 | Japan | 128/1 R |
| 0058947 | 12/1982 | Japan | 128/1 R |
| 0139936 | 8/1984 | Japan | 604/4 |

OTHER PUBLICATIONS

*Introduction to Immunology*, John W. Kimball, Macmillan Publishing Co., Inc., New York; 1983, pp. 233–234, 246.

Primary Examiner—C. Fred Rosenbaum
Assistant Examiner—Corrine Maglione
Attorney, Agent, or Firm—Armstrong, Nikaido, Marmelstein, Kubovcik & Murray

[57] ABSTRACT

A medical device, particularly a filter, cannula, catheter, or implant made of plastic or plastic-coated metal or glass for fixing disease-causing microorganisms, particularly viruses, bacteria, and fungi as well as pathogenic metabolic products, toxins, lipoid substances, and drugs, wherein the plastic surface is provided (firmly attached thereto or covalently bound therewith):

a) homologous or monoclonal immunoglobulins, preferably those that have been afterpurified by affinity chromatography in the classes G1, G2, G3, and/or G4 and/or IGM, IGE, IGD and/or IGA and/or the F(ab)2 fragments thereof, preferably those that have been afterpurified by affinity chromatography, which are selectively active against the specific antigens or antigenic determinants of the respective disease-causing microorganisms, particularly viruses, bacteria, and fungi as well as pathogenic metabolic products, toxins, lipoid substances (e.g., lipids), and drugs, or b) gamma globulins, particularly heterologous gamma globulins, which are active against the most widely differing antigens or antigenic determinants of the disease-causing microorganisms concerned, particularly viruses, bacteria, and fungi.

5 Claims, No Drawings

METHOD OF PURIFYING WHOLE BLOOD

This application is a continuation of application Ser. No. 220,880 filed June 22, 1988, now abandoned, which is a continuation of application Ser. No. 881,416 filed July 2, 1986 now abandoned.

BACKGROUND OF THE INVENTION

1. Field of the Invention

The invention relates to a medical device, more particularly a filter, a cannula, a catheter or an implant, of plastic or plastic-coated metal or glass, which can be used inside or outside the human body to fix, and thereby to render harmless, disease-causing microorganisms, particularly viruses, bacteria, and fungi, as well as pathogenic metabolic products, toxins, lipoid substances, and drugs. The invention relates in particular to filters for the separation of disease-causing microorganisms, especially viruses, bacteria, and fungi, as well as pathogenic metabolic products, lipoid substances, toxins, and drugs from blood, as well as cannulas, catheters, and implants that can be introduced into the human body without the risk of infection.

2. Description of the Prior Art

Unexamined West German Patent Application DE-OS 32 28 849 discloses a medical device to be introduced into the body and having a coating which releases microbicidal metal ions. The metal ions are gold, silver, and copper ions.

With devices to be introduced into the human body, e.g., probes, it is also well known in the art to treat the surface of the probes with iodine compounds to reduce the risk of infection.

However, the prior art processes have proved to be inadequate in practice, because the applied agents such as precious metal ions, iodine compounds, or antibiotics are released from the coated material and thus the risk of infection is reduced only during a brief period. Also, any microorganisms that may be present react metabolically with the released substances, so that resistances and the like may be developed. In addition to the risk of infection, the formation of a fibrin layer on the surface of intravasal catheter has a deleterious effect on catheters to be introduced into the body. The proposed solution, i.e., to coat intravasal catheters with heparin in order to avoid the usual fibrin deposits, has likewise proved unsuccessful.

The increasing development of multiple resistance and the high financial cost associated therewith call for a new protective system. Therefore, catheters, cannulas, or implants that can remain in the body for long periods of time without the risk of infection are desired.

Furthermore, efforts have been made for a long time in the medical field to develop treatment methods for highly toxic, viral or bacterial infectious diseases, such as AIDS, hepatitis A, hepatitis B, non-A, non-B hepatitis, tetanus, and genetically conditioned metabolic disorders, e.g., phenylketonuria, or other intoxications such as, for example, with digitalis glycosides or barbiturates. Success, however, has been very limited. Interferon has been used as an established agent against viral diseases, but the efficacy of interferon treatment is very limited, because the spectra of the various interferons and the organ specificities thereof differ considerably.

Despite substantial outlays of material and work involved, the therapeutic results to date have also been limited with respect to bacterial diseases, such as tetanus, genetically conditioned metabolic disorders such as phenylketonuria, or intoxications, e.g. with digitalis glycosides or barbiturates.

Accordingly, a simple method was desired by which the disease-causing viruses, bacteria, fungi, pathogenic metabolic products, lipoid substances (particularly lipids), and drugs can be removed from, or filtered out, of the blood. However, the treatment method is to be designed such that the disease-causing substances or other substances, if they can be removed by filtration, do not remain in the blood as an antigen-antibody complex.

Accordingly, the invention has as its object the development of a medical device, particularly cannulas, catheters, and implants as well as filters made of plastic or plastic-coated metal or glass, by means of which disease-causing microorganisms, particularly viruses, bacteria, and fungi as well as pathogenic metabolic products, toxins, lipoid substances (especially lipids), and drugs in blood, particularly human blood, can be fixed inside or outside the human body in such a way that the infections caused thereby can be prevented with assurance, or that these undesirable substances can be reliably removed from the blood without risk.

SUMMARY OF THE INVENTION

It has now been found that this object can be achieved with a medical device, particularly a filter, cannula, catheter, or implant made of plastic or plastic-coated metal or glass for fixing disease-causing microorganisms, particularly viruses, bacteria, and fungi as well as pathogenic metabolic products, toxins, lipoid substances, and drugs, said device being characterized by the fact that the plastic surface is provided with (firmly attached thereto or covalently bound therewith):

a) homologous or monoclonal immunoglobulins, preferably those that have been afterpurified by affinity chromatography in the classes G1, G2, G3, and/or G4 and/or IGM, IGE, IGD and/or IGA and/or the F(ab)2 fragments thereof, preferably those that have been afterpurified by affinity chromatography, and which are selectively active against the specific antigens or antigenic determinants of the disease-causing microorganisms concerned, particularly viruses, bacteria, and fungi as well as pathogenic metabolic products, toxins, lipoid substances (e.g., lipids), and drugs, or b) gamma globulins, particularly heterologous gamma globulins, which are active against the most widely differing antigens or antigenic determinants of the disease-causing microorganisms concerned, particularly viruses, bacteria, and fungi.

Used as plastic materials in medical technology are common plastics, for example, polyolefins, polyesters, polyethers, polyamides, polyimides, polyurethanes, polyvinyl chlorides, polysulfones, polystyrenes, polyacrylates, polymethacrylates, polypropylenes, polyvinylpyrrolidones, fluoropolymers, plastics based on acrolein, derivatives of said compounds, mixtures, and copolymers thereof, as well as silicone rubber. Polystyrene- and polyurethane-based plastics are particularly suitable. Also suitable for this purpose is glass that has been pretreated, for example, with acrolein, such as Controlpore glass (a product of Sigma), and the like. The surface of the plastic employed in accordance with the teachings of the invention is preferably pretreated with gamma rays or ozone, because the adhesive strength of the applied immunoglobulins or gamma globulins is increased thereby. Pretreatment of the plastic surface or glass surface by ion etching or by acrolein or an acid is another option. Particularly advantageous is the application of a coupling agent or spacer to the plastic surface to improve the adhesive strength of immunoglobulines or gamma globulins to the plastic surface, particularly those from the group of cyanogen bromide, thiophosgene, and thionyl chloride, which can also be used to activate the plastic surface and can also produce a covalent bond between substrate and globulin.

Spacers are molecular connectors for increasing the distance between the surface of the carrier material and the immunoglobulin. One skilled in the art is familiar with the term spacer. The covalent bond is effected, for example, with cyanogen bromide or thiophosgene.

DETAILED DESCRIPTION OF THE INVENTION

The invention will now be described in greater detail with reference to two preferred embodiments, but is not limited thereto, namely a filter for the separation of disease-causing microorganisms, particularly viruses, bacteria, and fungi as well as pathogenic metabolic products, lipoid substances (e.g., lipids), and drugs from blood, on the one hand, and catheters, cannulas, or implants which can remain within the body for a long time without risk of infection, on the other.

A filter of the type indicated in the introduction has now been developed, which is characterized by the fact that it is made of a plastic which can be perfused by blood and is physiologically safe, whereby the plastic surface of the filter is provided with homologous or monoclonal immunoglobulines, preferably those that have been afterpurified by affinity chromatography in the classes G1, G2, G3 and/or G4, and/or IGM, IGE, IGD and/or IGA and are selectively active against the specific antigens or antigenic determinants of the particular viruses, bacteria, fungi, pathogenic metabolic products, toxins, lipoid substances, or drugs. The immunoglobulins are applied securely to the surface of the filter by adsorption or by means of a coupling agent or covalent bond.

Preferably, the plastic surface of the filter is one that has been pretreated with gamma rays or ozone, because this increases the adhesive strength of the immunoglobulins applied by means of an impregnation process. Adherence of immunoglobulins of classes G1, G2, G3 and/or G4 and/or IGM, IGE, IGD and/or IGA to the plastic surface of the filter can be enhanced further by applying, after surface treatment with gamma rays or with ozone, a coupling agent or acrolein to the surface to improve the adherence of the immunoglobulins to the plastic surface, especially by the formation of a covalent bond.

The filter may be a compact filter, membrane filter, packed filter, molecular sieve filter, or capillary filter. Particularly suitable is also an enclosure filled with spherical, annular, saddle-shaped, spiral, stellate, cylindrical or reticulate plastic particles. The capillary blood filters of known construction can also be used for the purposes of the invention.

The separation of disease-causing substances or other substances from the blood is effected in a manner such that blood from the body is pressed into the filter by means of a blood pump, during which the filtration rate is approximately 6 to 30 ml of blood per minute. The total blood volume of the patient with, for example, AIDS, hepatitis A, hepatitis B, non-A, non-B hepatitis, viral encephalitis, or some other highly pathogenic treatment-resistant bacterial or mycotic infection or a genetically conditioned, virus-induced, or genetic metabolic disorder such as phenylketonuria or an intoxication, is passed across the filter of the invention as in hemodialysis.

The antigen-antibody complex formation specific in each case is effected by means of the homologous or monoclonal immunoglobulins applied to the plastic surface of the filter incorporating the invention, i.e., the particular viruses, bacteria, pathogenic metabolic products, toxins, lipoid substances, or drugs are filtered out of the blood flowing through the filter by binding to the antibodies.

The abovementioned pathogenic or other pathogenic substances or organisms are immobilized in this manner on the filter. Thus, the antigen-antibody complex is not removed from the blood stream.

The reaction surface, i.e., the size of the filter surface coated with antibodies, is determined on the basis of the filter concerned. The blood purified in this manner is subsequently retransfused.

Blood washing* is carried out at about 37 degrees Celsius and is repeated two to three times for disease-causing bacteria and fungi and five to six times for the separation of disease-causing viruses, until the pathogens are totally removed from the blood. For the removal of viruses, the blood washing must be repeated after cell lysis, i.e., the particular cycle of lysis which manifests itself in a corresponding rise in temperature is used as an indication for the next blood washing. The repeated use of blood washing in the case of viruses bound to DNA is necessary, because these viruses react with the antibodies on the surface of the filter only after the corresponding cell lysis.

* Blutwaesche: According to Bunjes, this word means "lavage of the blood, systemic lavage, hematocatharsis, washing-out of the blood by means of the artificial kidney." However, according to our medical consultants, "Blutwaesche" as applied to this invention is none of these, nor is it "hemodialysis", which is described in our German medical dictionaries as "The removal of certain elements from the blood by virtue of the difference in the rates of their diffusion through a semipermeable membrane". We decided to translate it literally as "blood washing", which makes sense, according to our consultants, since it is related to the AIDS problem.

In highly pathogenic, treatment-resistant microorganisms and in intoxications not associated with DNA, one or two passages of the infected blood through the novel filter are generally sufficient. In genetically conditioned metabolic disorders, blood washing is to be repeated in accordance with the resulting concentration of the pathogenic metabolic products.

The immunoglobulins G1, G2, G3 and/or G4 and/or IGM, IGE, IGD and/or IGA are applied to the plastic surface of the filter in the appropriate immunoglobulin solution. The impregnation times are approximately 1 to 10 hours. The filter occupied by the immunoglobulins is then washed with a phosphate buffer solution to wash away excess immunoglobulines, after which the filter is dried.

As an alternative to the abovementioned impregnation process, these immunoglobulins can be applied over activated plastics via cyanogen bromide, thiophosgene, or thionyl chloride following gamma irradiation by means of coupling agents or a similar process producing covalent bonds.

In the past, blood washing has been effected by reacting full antibodies with the particular antigens of the substances to be removed to form an antigen-antibody complex. Optimization of this process is particularly achieved when treating infectious diseases, such as AIDS, by pretreating in the immunoglobulins with pepsin, which results in the cleavage of the F(ab)2 and Fc fragment. The Fc fragment is then separated by chromatography. Sepharose CL6B is used for this purpose. In so doing, the activated gel is left to react for a period of 40-54 hours at 2-10 degrees Celsius, resulting in the quantitative separation of the Fc fragment. The F(ab)2 fragments thus obtained are now reacted with the plastic surfaces. Glass beads are used as carriers in addition to polar plastics.

The significance of blood washing by means of the separated immunoglobulins F(ab)2 is based on the following:

1. When whole blood reacts with immunoglobulin that has not been separated, several nonspecific bindings to the Fc fragment occur in addition to the specific antigen binding to the F(ab)2 fragment, where the complement factors inter alia represent an important group in this case. In terms of practical application, this means that substances important for the body's own resistance to infections are removed from the already weakened patient. Phagocytosis of the microorganisms concerned is appreciably reduced.

The problems of any thrombus formation when carrying out the blood washing described herein is precluded by the fact that 5-25% of the coated reaction surface is occupied not by the F(ab)2 fragment, but by heparin. In contrast to F(ab)2 molecules, which are covalently bound, heparin is applied by adsorption. The filtration unit employed for the blood washing is to be sterilized very carefully with ethylene oxide or by gamma irradiation because of the protein characteristics of the active antibodies, and it cannot be guaranteed that inactivation of the active antibodies will not occur.

The following new sterilization procedure is an option for the absolute avoidance of inactivation:

A mixture of heterologous immunoglobulins is placed in a physiologic solution (e.g., Ringer's solution). The filtration unit is charged with this solution and left for a period of 10-30 minutes. Because of the heterologous immunoglobulins, an antigen-antibody reaction of different avidity occurs with microorganisms or pyrogens that may be present. The size of the antigen-antibody complex requires that the thusly bound microorganism or pyrogen be washed out in three subsequent washes with a physiologic solution without antibodies.

Medical cannulas, catheters or implants embodying the invention are characterized by adsorption of gamma globulins, particularly heterologous gamma globulins, on the plastic surface.

Thus, the basic consideration is concerned with the fact that all microorganisms, whether bacteria or viruses, have a number of antigenic determinants at their disposal. Within the body, these cause the production of specific antibodies, which form the antigen-antibody complex necessary for recovery. The microorganisms are immobilized solely by the formation of the antigen-antibody complex on the plastic surface. This prevents the microorganisms from gaining further ground in the body. The antigen-antibody complex formation on the surface of the plastic can be achieved in vivo with an appropriate coating of implants, catheters, cannulas, and probe materials, as well as artificial organs, with gamma globulins. This means that microorganisms are bound by contact with the gamma globulins due to their antigenic properties, thereby inhibiting their movement. Thus, further penetration or multiplication in the body is precluded.

Since the antibodies or gamma globulins are firmly, preferably covalently, bound to the plastic surface and are not released to the medium, no metabolic transformation will occur, because the effect described above is an immobilizing, rather than a bactericidal or bacteriostatic, effect.

The all-around coating of the catheters, cannulas, and implants described herein also inhibits retrograde microbial migration on the outer and inner wall of the these articles.

Preferably, the plastic surface or plastic material consists of polypropylene, polyurethane, polyvinylpyrrolidone, polyacrylate, polymethacrylate, polyamide, or copolymers thereof.

The plastic surface is treated prior to the application of the gamma globulins by means of gamma rays, ion etching, ozone etching, or with a solution with a pH of 7.5 to 10.5 or with acrolein, in order to improve the adhesive strength of gamma globulins to the surface. Depending on the plastic starting material, the treatment is carried out at a pH of 7.5 to 10.5, the reaction time being 5 to 10 minutes likewise depending on the plastic. The plastic surface to be coated can also be roughened, particularly by alkylation treatment with methyl iodide.

In addition to the roughening of the surface, the plastic can also be treated with a coupling agent, particularly cyanogen bromide, thiophosgene, or thionyl chloride, which also causes the gamma globulins to adhere to the plastic surface, especially via the formation of a covalent bond.

Another option for application to the plastic surface of cannulas, catheters, implants, probes, vascular prostheses, and cardiac pacemakers is the impregnation of the plastic surface pretreated with an appropriate roughening operation, with the saturated gamma globulin solution. The impregnation of the plastic surface is carried out at approximately 20° to 40° C., and for a period of about 1 to 10 hours.

After the binding by means of a coupling agent or after the adsorption of the gamma globulins on the plastic surface, the carrier materials are rinsed with a phosphate buffer solution to wash out excess gamma globulins. The materials are then dried at an appropriate temperature (20° to 40° C. for 8 to 24 hours) and sterilely packed.

Only polar plastics with the necessary physical properties, such as elasticity and fracture toughness, are used as plastic materials for introduction into the body.

A major aspect of the novel medical cannulas, catheters, or implants is the use of preferably heterologous gamma globulins, because only coating with this type of gamma globulins ensures the possibility of binding all the microorganisms.

We claim:

1. A method for purifying whole blood which comprises contacting whole blood containing a pathogenic microorganism or a metabolic product of a pathogenic microorganism with a plastic surface having attached thereto F(ab)$_2$ fragments from a homologous or monoclonal immunoglobulin selectively active against a specific antigen or antigenic determinant of the pathogenic microorganism or the metabolic product of the pathogenic microorganism, wherein the F(ab)$_2$ fragments are free of Fc fragments, to separate the pathogenic microorganism or the metabolic product of the pathogenic microorganism from the whole blood contacted with said plastic surface.

2. A method according to claim 1, wherein the F(ab)$_2$ fragments are covalently bound to the plastic surface.

3. A method according to claim 1, wherein the F(ab)$_2$ fragments were obtained by enzymatically cleaving the immunoglobulin to form F(ab)$_2$ and Fc fragments and wherein the Fc fragments were separated before the F(ab)$_2$ fragments were attached to the plastic surface.

4. A method according to claim 1, wherein the immunoglobulin is at least one of G1, G2, G3, G4, IGM, IGE, IGD or IGA immunoglobulin.

5. A method for purifying whole blood which comprises:
   a) withdrawing whole blood containing a pathogenic microorganism or a metabolic product of a microorganism from a body,
   b) contacting the whole blood removed from the body with a plastic surface having attached thereto F(ab)$_2$ fragments, from which the Fc fragments have been separated, of a homologous or monoclonal immunoglobulin selectively active against a specific antigen or antigenic determinant of the pathogenic microorganism or the metabolic product of the microorganism, and
   c) returning the thus contacted whole blood to the body.

* * * * *

UNITED STATES PATENT AND TRADEMARK OFFICE
CERTIFICATE OF CORRECTION

PATENT NO. : 5,061,237

DATED : October 29, 1991

INVENTOR(S) : Reiner Gessler et al

It is certified that error appears in the above-identified patent and that said Letters Patent is hereby corrected as shown below:

On the cover page, Item [21], "420,770" should read -- 420,700 --.

Signed and Sealed this

First Day of June, 1993

Attest:

Attesting Officer

MICHAEL K. KIRK

Acting Commissioner of Patents and Trademarks